(12) United States Patent
Splieth et al.

(10) Patent No.: US 8,257,363 B2
(45) Date of Patent: Sep. 4, 2012

(54) EXPANDABLE REVERSE SHOULDER TRIAL

(75) Inventors: Roy Philip Splieth, Central Valley, NY (US); James David Lorek, Lincoln Park, NJ (US); Shawn Michael Kroll, Waldwick, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1180 days.

(21) Appl. No.: 11/974,424

(22) Filed: Oct. 12, 2007

(65) Prior Publication Data
US 2009/0099662 A1 Apr. 16, 2009

(51) Int. Cl.
*A61B 17/58* (2006.01)
*A61B 17/60* (2006.01)
*A61F 2/00* (2006.01)

(52) U.S. Cl. .................. 606/102; 606/91; 623/19.11
(58) Field of Classification Search .................. 606/102, 606/91; 623/17.11–17.14
See application file for complete search history.

(56) References Cited

U.S. PATENT DOCUMENTS

| | | |
|---|---|---|
| 3,102,536 A | 9/1963 | Rose |
| 3,806,957 A | 4/1974 | Shersher et al. |
| 3,978,528 A | 9/1976 | Crep |
| 4,030,143 A | 6/1977 | Elloy et al. |
| 4,040,131 A | 8/1977 | Gristina |
| 4,693,723 A | 9/1987 | Gabard et al. |
| 5,462,563 A | 10/1995 | Shearer et al. |
| 5,569,263 A | 10/1996 | Hein |
| 5,658,340 A | 8/1997 | Muller et al. |
| 5,702,457 A | 12/1997 | Walch et al. |
| 5,741,335 A | 4/1998 | Gerber et al. |
| 6,033,439 A | 3/2000 | Camino et al. |
| 6,120,542 A | 9/2000 | Camino et al. |
| 6,206,925 B1 | 3/2001 | Tornier |
| 6,228,120 B1 | 5/2001 | Leonard et al. |
| 6,368,352 B1 | 4/2002 | Camino et al. |
| 6,508,841 B2 | 1/2003 | Martin et al. |

(Continued)

FOREIGN PATENT DOCUMENTS
DE 10335442 2/2005

(Continued)

OTHER PUBLICATIONS

Reverse Shoulder Prosthesis, Surgical Technique, Encore, 2005.

(Continued)

*Primary Examiner* — Andrew Yang
(74) *Attorney, Agent, or Firm* — Lerner, David, Littenberg, Krumholz & Mentlik, LLP

(57) ABSTRACT

An expandable shoulder trial for a reverse shoulder system is described. The trial includes a rotatably adjustable insert housed within a humeral cup. The insert has a proximal end and a distal end, the proximal end having a concave recess therein adapted to receive a glenosphere prosthesis. The distal end of the insert includes a shaft, the shaft having a helical groove disposed on at least a portion thereof. A distal end of the humeral cup is inserted in a humeral stem. The humeral cup has a proximal end including a recess therein, the recess defined by a circular wall. A guide pin protrudes from the circular wall and is adapted to engage the helical groove of the shaft of the insert. The proximal end of the insert may rotate along an axis toward the proximal end of the humeral cup and along the same axis away from the proximal end of the humeral cup.

25 Claims, 19 Drawing Sheets

U.S. PATENT DOCUMENTS

| | | | |
|---|---|---|---|
| 6,673,114 B2 * | 1/2004 | Hartdegen et al. | 623/19.12 |
| 6,761,740 B2 | 7/2004 | Tornier | |
| 6,790,234 B1 | 9/2004 | Frankle | |
| 6,887,277 B2 | 5/2005 | Rauscher et al. | |
| 6,899,736 B1 | 5/2005 | Rauscher et al. | |
| 6,953,478 B2 | 10/2005 | Bouttens et al. | |
| 6,969,406 B2 | 11/2005 | Tornier et al. | |
| 6,986,790 B2 | 1/2006 | Ball et al. | |
| 7,097,663 B1 | 8/2006 | Nicol et al. | |
| 7,108,405 B2 | 9/2006 | Matts et al. | |
| 7,169,184 B2 | 1/2007 | Dalla Pria et al. | |
| 7,175,663 B1 | 2/2007 | Stone | |
| 7,238,208 B2 | 7/2007 | Camino et al. | |
| 7,241,314 B1 | 7/2007 | Winslow | |
| 7,309,360 B2 | 12/2007 | Tornier et al. | |
| 7,329,284 B2 | 2/2008 | Maroney et al. | |
| 7,425,214 B1 * | 9/2008 | McCarthy et al. | 606/89 |
| 7,445,638 B2 | 11/2008 | Beguin et al. | |
| 7,462,197 B2 | 12/2008 | Tornier et al. | |
| 7,608,109 B2 | 10/2009 | Dalla Pria | |
| 7,611,539 B2 | 11/2009 | Bouttens et al. | |
| 7,621,961 B2 | 11/2009 | Stone | |
| 7,678,150 B2 | 3/2010 | Tornier et al. | |
| 2002/0120339 A1 | 8/2002 | Callaway et al. | |
| 2003/0114933 A1 | 6/2003 | Bouttens et al. | |
| 2003/0158605 A1 | 8/2003 | Tornier | |
| 2004/0220674 A1 | 11/2004 | Pria | |
| 2004/0267370 A1 | 12/2004 | Ondrla | |
| 2005/0128755 A1 | 6/2005 | Matts et al. | |
| 2005/0256583 A1 | 11/2005 | Bouttens et al. | |
| 2005/0278032 A1 | 12/2005 | Tornier et al. | |
| 2005/0288681 A1 | 12/2005 | Klotz et al. | |
| 2006/0200247 A1 | 9/2006 | Charrois | |
| 2007/0156246 A1 | 7/2007 | Meswania et al. | |
| 2007/0173945 A1 | 7/2007 | Wiley et al. | |
| 2007/0179624 A1 | 8/2007 | Stone et al. | |
| 2007/0244563 A1 | 10/2007 | Roche et al. | |
| 2008/0221622 A1 | 9/2008 | Triplett et al. | |
| 2008/0228281 A1 | 9/2008 | Forrer et al. | |
| 2008/0275507 A1 | 11/2008 | Triplett et al. | |
| 2009/0099662 A1 | 4/2009 | Splieth et al. | |
| 2009/0149961 A1 | 6/2009 | Dallmann | |
| 2009/0164021 A1 | 6/2009 | Dallmann | |
| 2009/0171462 A1 | 7/2009 | Poncet et al. | |
| 2009/0192621 A1 | 7/2009 | Winslow et al. | |
| 2009/0210065 A1 | 8/2009 | Nerot et al. | |
| 2009/0281630 A1 | 11/2009 | Delince et al. | |
| 2010/0087927 A1 | 4/2010 | Roche et al. | |
| 2010/0161065 A1 | 6/2010 | Williams, Jr. et al. | |
| 2010/0161066 A1 | 6/2010 | Iannotti et al. | |
| 2010/0222886 A1 | 9/2010 | Wiley et al. | |
| 2010/0228352 A1 | 9/2010 | Courtney, Jr. et al. | |

FOREIGN PATENT DOCUMENTS

| | | |
|---|---|---|
| EP | 1520560 | 4/2005 |
| EP | 2047827 A1 | 4/2009 |
| FR | 2689756 | 10/1993 |
| GB | 2405346 A | 3/2005 |
| WO | 2005032430 | 4/2005 |
| WO | 2007039820 | 4/2007 |
| WO | 2007084939 | 7/2007 |

OTHER PUBLICATIONS

Mode Operatoire, Operative Technique, Arrow, date not known.
Trabecular Metal Reverse Shoulder System, Zimmer, date not known.
Delta Reverse Shoulder System, Surgical Technique, DePuy 2004.
European Search Report, EP 10156704, dated Jun. 14, 2010.
European Search Report, EP 08166202, Jan. 27, 20009.

* cited by examiner

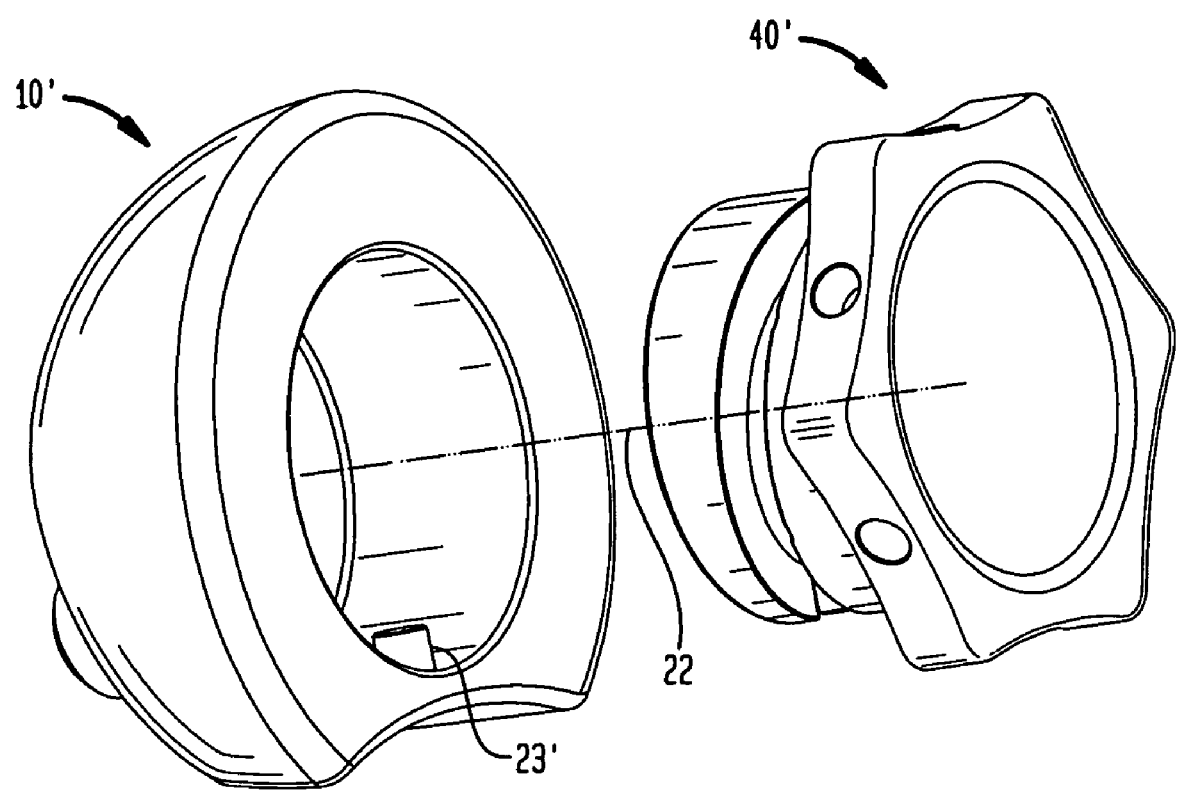

EXPANDABLE REVERSE SHOULDER TRIAL

FIELD OF THE TECHNOLOGY

The present invention relates to an expandable reverse shoulder trial for reverse shoulder athroplasty (RSA), and in particular it relates to such a trial including an insert that rotatably engages a humeral cup.

BACKGROUND OF THE INVENTION

The successful outcome of RSA depends greatly on proper soft tissue tension. Since the rotator cuff is either absent or severely compromised and irreparable, the stability of the shoulder joint comes from significant deltoid tension holding the ball and socket joint together.

Existing reverse shoulder systems require a surgeon to pick a trial liner and reduce the shoulder joint with that liner assembled into a humeral cup. If the correct liner is chosen, the soft tissue tension is significant, requiring the surgeon to apply extreme force to the humerus and surrounding soft tissues to reduce the joint. If no additional damage is done during this reduction process, the joint must then be dislocated to allow the surgeon to implant a joint replacement prosthesis.

Dislocation can often be more difficult than reduction and RSA patients often have compromised bone stock and/or soft tissue. The extreme force required to dislocate the joint again may put the patient at risk for other injury and soft tissue trauma. Furthermore, current systems require the surgeon to use a trial and error approach in establishing proper soft tissue tension. This often takes several attempts before adequate stability is achieved.

There currently exists a need for an adjustable trial including an insert that rotatably engages a humeral cup. The insert may first be inserted into the humeral cup and then rotated into a fully collapsed or neutral position. Such a device may allow a surgeon to easily reduce the shoulder joint. Preferably, the insert may then be advanced to a position where optimal deltoid tension is achieved. At this position, the insert and humeral cup are preferably calibrated such that the surgeon may determine a liner thickness corresponding to a dialed position of the insert with respect to the humeral cup. The terms "dialed position" or "dial in" indicate the distance between a proximal end of the insert and a proximal end of the humeral cup. This distance or liner thickness is measured by indications on the insert, such as calibration marks and/or attachment locations in reference to a marker on the humeral cup. This will be further explained in the detailed description.

The surgeon may also perform range of motion ("ROM") and joint stability analyses during calibration of the trial. Preferably, the surgeon may then easily collapse the trial back to the neutral position and simply dislocate the joint. Further, the trial may also be preferably expanded prior to joint reduction and collapsed prior to joint dislocation repeatedly, depending on surgeon preference. Once the trial has been optimized, a surgeon preferably records the dialed position of the expanded trial. This measurement should preferably be the liner thickness. If this measurement does not correspond to the size of a particular liner in the system, the surgeon may select a next larger sized liner. At this time, the surgeon may remove the trial and then implant a prosthesis including a humeral cup and the selected liner.

SUMMARY OF THE INVENTION

The present invention greatly eases the reduction and dislocation of a shoulder joint during trialing because the surgeon may custom fit a trial to a patient after the joint has been reduced. This will greatly decrease the patient's exposure to intraoperative soft or hard tissue injuries related to extreme forces required to reduce and dislocate the joint. Moreover, the preferred one-step trialing approach of the present invention will also decrease surgical time, which is healthier for the patient and more efficient for the surgeon and hospital. Preferably, the expandable trial also decreases the size and cost of the overall instrument set, since only one trial per glenosphere diameter is generally required.

A main distinguishing characteristic of the adjustable trial from prior art devices is the fact that an insert may be first inserted into a humeral cup and then rotated into a collapsed or neutral position. This preferably allows the surgeon to easily reduce the joint. The trial, including the insert and humeral cup may then be expanded into a second position wherein optimal deltoid tension is preferably achieved. Here, the trial is calibrated such that the surgeon can determine which liner thickness corresponds to the dialed position on the trial.

Following ROM and joint stability analysis, the surgeon can easily collapse the trial back to the neutral position and simply dislocate the joint. The trial may also be expanded prior to joint reduction and collapsed prior to joint dislocation repeatedly, depending on surgeon preference.

The purpose of the present invention is to allow the surgeon to reduce the reverse shoulder trial and surrounding soft tissues into a relaxed state and/or dislocate a reduced shoulder joint while in a relaxed state. This will greatly ease the reduction of the joint. Once reduced, the surgeon may then "dial in" the appropriate liner thickness to achieve proper soft tissue tension. The trial is preferably designed to expand in discreet increments which correspond to liner prostheses that are available in multiple thicknesses. After a liner prosthesis is selected, it is then implanted with a humeral cup prosthesis.

An example of a surgical technique for the expandable reverse shoulder trial of the present invention is as follows:

Step 1: Resect the proximal humerus at a height determined by a typical humeral resection guide and surgical technique. At this point the surgeon may move to glenoid preparation (step 5) or continue with humerus preparation.

Step 2: Prepare the humerus distally in a standard fashion first using intramedullary reamers of increasing size according to surgeon preference.

Step 3: Prepare the proximal humerus using broaches of increasing size. Preferably, starting with a broach that is smaller than the final prosthesis based on preoperative templating.

Step 4: Perform calcar planing to prepare the proximal humerus to ensure proper seating of a humeral cup into the humeral stem and/or perform proximal reaming to create a seat for the cup. A trial humeral cup may also be inserted to assess seating and interference. The cup trial should be removed prior to preparing the glenoid surface.

Step 5: Target the center of the glenoid using the centering guide and drill a centering hole. Insert a guide-wire or guide pin into the centering hole and ream the glenoid face progressively until sub-chondral bone is thoroughly exposed.

Step 6: Place and attach a baseplate on the glenoid face in a desired location.

Step 7: Select an appropriate glenosphere trial and attach to the baseplate.

Step 8: Select an expanding trial including an insert having a recess diameter matching the glenosphere trial diameter. Ensure that the expanding trial is in the fully collapsed or neutral position and insert the trial assembly into a tapered bore in the humeral broach or stem. The joint may now be reduced into a laxed state. Deltoid and remaining cuff tension can then be dialed in by expanding the trial. Laxity, ROM and stability can now be evaluated with the trial components in place. Trialing can also be accomplished by repeatedly reducing the shoulder joint at a specific thickness which the surgeon has dialed in, evaluating the fit and function, collapsing the trial, and dislocating the shoulder.

Step 9: If different components (diameter etc.) are desired, substitutions may be made prior to implanting the prostheses. Once the trial has been optimized, the dialed thickness of the expanded trial is preferably recorded. This measurement preferably will be the thickness of the liner prosthesis.

Step 10: Remove the trial and implant the prostheses.

These steps are an exemplary method of the invention. It is to be understood that modifications can be made to these steps or some of these steps may not be performed without departing from the spirit and scope of the present invention.

As used herein, when referring to bones or other parts of the body, the term "proximal" means closer to the heart and the term "distal" means more distant from the heart. The term "inferior" means lower or bottom and the term "superior" means upper or top. The term "anterior" means towards the front part of the body or the face and the term "posterior" means towards the back of the body. The term "medial" means toward the midline of the body and the term "lateral" means away from the midline of the body.

A first aspect of the present invention is an expandable shoulder trial having an insert including a proximal end and a distal end, the proximal end having a concave recess therein. Preferably, the distal end of the insert includes a shaft, the shaft having a helical groove disposed on at least a portion thereof. Preferably, the trial further includes a humeral cup having a proximal end including a recess therein, the recess defined by a circular wall for securing the insert shaft. A guide pin preferably protrudes from the circular wall into the recess, the guide pin adapted to engage the helical groove of the shaft of the insert.

Preferably, the proximal end of the insert may be rotatably adjusted in a first axial direction toward the proximal end of the humeral cup to collapse the trial and alternatively in an opposite second axial direction away from the proximal end of the humeral cup to expand the trial.

In accordance with one embodiment of this first aspect of the present invention, the helical groove of the shaft preferably allows the insert when rotated to move in the first and second axial directions as the insert is rotated in only a first direction (i.e. clockwise or counter-clockwise direction). Preferably, the thickness and/or axial distance between the proximal end of humeral cup and the proximal end of the insert is adjusted by rotating the insert in either the first and or the second directions.

In accordance with yet another embodiment of this first aspect of the present invention, the proximal end of the insert preferably includes an outer face having a plurality of calibration marks arranged thereon.

In accordance with still yet another embodiment of this first aspect of the present invention, the outer face of the insert preferably includes a plurality of attachment locations adapted to engage an adjustment tool for rotating the insert.

In accordance with still yet another embodiment of this first aspect of the present invention, the proximal end of the humeral cup includes a front face having a marker arranged thereon. Preferably, the axial distance between the proximal end of humeral cup and the proximal end of the insert is indicated by the calibration marks on the insert in reference to the marker on the humeral cup.

The trial of the present invention may also be provided as an expandable shoulder trial including a humeral cup having an axis, the humeral cup including a recess defining a substantially circular wall about the axis, the circular wall having a guide portion extending outwardly therefrom. Preferably, the trial further includes an insert having a proximal end and a distal end, the proximal end of the insert having a concave recess disposed thereon, the distal end having a shaft extending therefrom towards the proximal end, the shaft of the insert preferably received in the recess of the cup. Preferably, the shaft includes a helical groove disposed on at least a portion thereof. Preferably, the guide portion is adapted to engage the helical groove of the shaft so that when the insert is rotatably adjusted the insert may move from a neutral position wherein the proximal end of the insert is substantially adjacent to the proximal end of the humeral cup, and into an expanded position wherein the proximal end of the insert is further away from the proximal end of the cup in the axial direction.

A second aspect of the present invention is an expandable shoulder trial including a humeral cup having a distal end portion coupled to a stem, the humeral cup further including a proximal end portion having a base and a circular wall defining a circular recess, the wall having a guide pin protruding therefrom. Preferably the trial further includes an insert having a proximal end portion and a distal end portion for insertion in the circular recess of the humeral cup, the distal end portion having a cam track extending toward the proximal end portion, the cam track adapted to receive the guide pin of the humeral cup. Preferably, the insert is rotatably adjustable along an axis in a first direction such that the distal end portion of the insert moves toward the base of the recess of the humeral cup.

In accordance with one embodiment of this second aspect of the present invention, the insert is rotatably adjustable along the axis in an opposite second direction wherein the distal end of the insert moves away from the base of the recess of the humeral cup.

In one aspect of a method of the present invention, the insert may be rotated in the first direction approximately 60° to reduce the distance between the proximal end of the humeral cup and the proximal end of the insert approximately 2 mm. Preferably, the insert includes an incremental stopping portion every 60° along the guide portion or cam-track of the shaft portion of the insert. As the insert is rotated in either a first or second direction the guide pin of the humeral cup may engage an incremental stopping portion of the insert. This may stop the insert from further rotation until a force great enough to overcome the friction between the guide pin and the incremental stopping portion is produced.

Generally, the present invention is an expandable reverse shoulder trial for RSA. In one aspect of the present invention, the trial is designed to take the place of a kit of trials and to provide the surgeon with greater intraoperative flexibility and ease of trialing during RSA. Prior art devices include trials of increasing thicknesses in "kit" form.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 8 shows an axis of the humeral cup of FIG. 2A aligned with an axis of the insert of FIG. 5A prior to assembly.

DETAILED DESCRIPTION

Figure 1A:
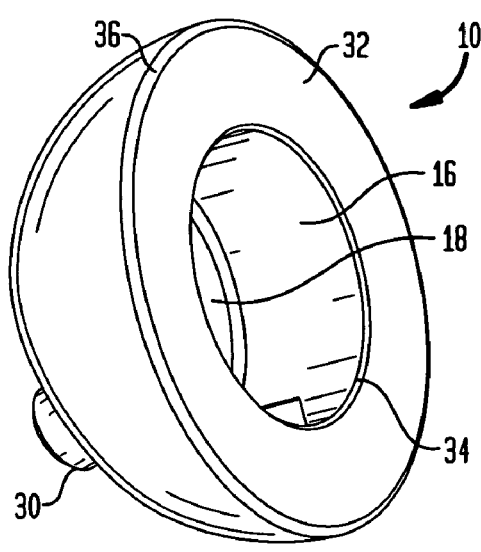
FIG. 1A is an isometric view of a humeral cup according to an embodiment of the present invention.
Figure 1B:
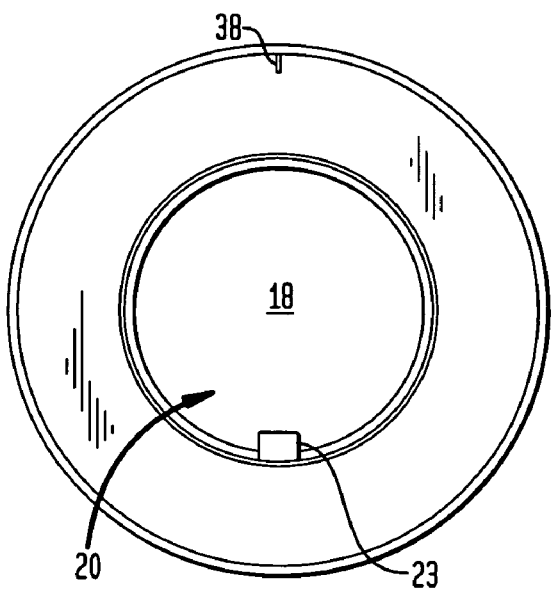
FIG. 1B is a front view of the humeral cup according to FIG. 1A.
Figure 1C:
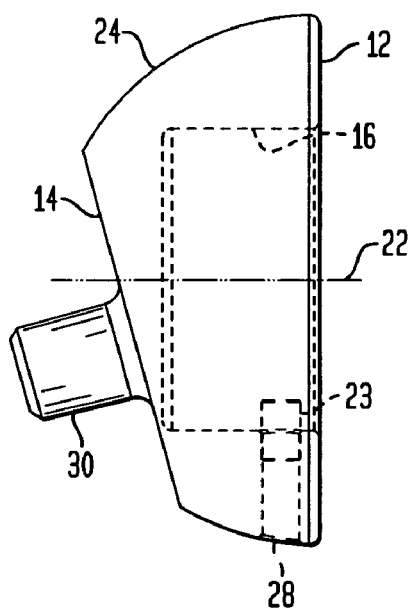
FIG. 1c is a side view of the humeral cup according to FIG. 1A.
Figure 1D:
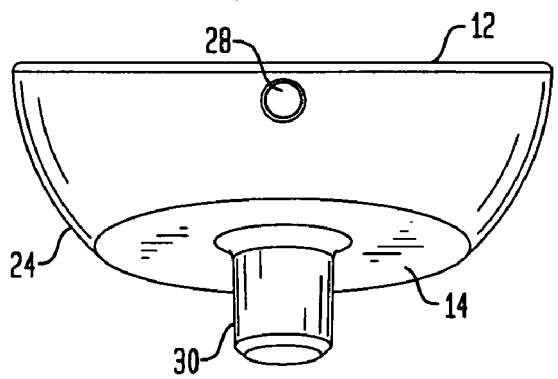
FIG. 1D is a bottom view of the humeral cup according to FIG. 1A.
Figure 2A:
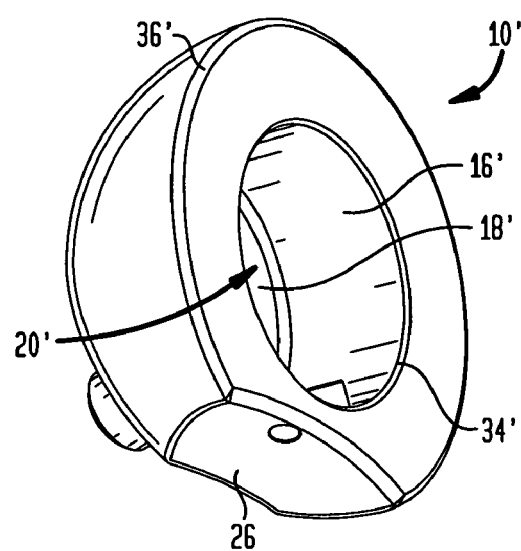
FIG. 2A is an isometric view of an alternative embodiment of a humeral cup according to the present invention.
Figure 2B:
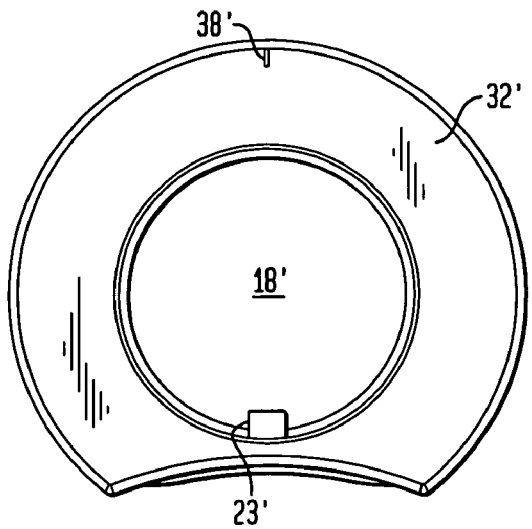
FIG. 2B is a front view of the humeral cup according to FIG. 2A.
Figure 2C:
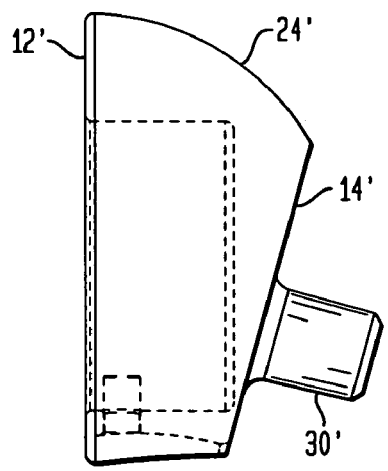
FIG. 2C is a side view of the humeral cup according to FIG. 2A.
Figure 2D:
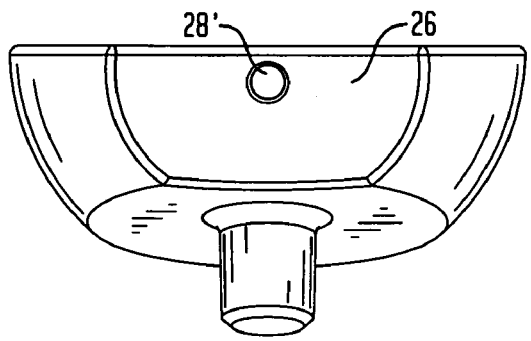
FIG. 2D is a bottom view of the humeral cup according to FIG. 2A.

Referring to FIGS. 1A-1D, there is shown an embodiment of a humeral cup of the present invention designated generally by reference numeral 10. As shown in those figures, cup 10 includes a proximal end 12 and a distal end 14. Cup 10 preferably further includes a circular wall 16 and a base 18 defining a recess 20. Recess 20 defines a central axis 22 as shown in FIG. 1C. Preferably, a guide portion 23 protrudes from wall 16. Guide portion 23 is preferably configured as a pin.

In the preferred embodiment, proximal end 12 and distal end 14 of cup 10 are not coplanar. Between distal end surface 14 and proximal end surface 12 is a hemispherical outer surface 24. In an alternative embodiment, as shown in FIGS. 2A-2D, a cup 10' further includes a concave surface 26 located between a proximal end surface 12' and a distal end surface 14'. Surface 26 faces medially and is preferably configured to allow for greater articulation of cup 10' with respect to a scapula bone after cup 10' has been trialed in the body. Cups 10 and 10' generally include all of the same features except for cup 10' including concave surface 26 and a partially hemispherical outer surface 24'.

As shown in FIGS. 2A-2d, surface 26 may include a bore 28' associated therewith. Bore 28' may initially extend from surface 26 through wall 16' into recess 20'. Generally, bore 28' is configured to receive the guide pin 23' therein. Preferably, guide pin 23' has an end which protrudes outwardly from wall 16' into recess 20'. After guide pin 23' is located in position, such as shown generally in FIGS. 2A-2C, bore 28' may be filled such that surface 26 is a curved flat surface throughout.

Preferably, distal end 14, 14' of cup 10, 10' includes a trunion 30, 30' protruding distally therefrom. Trunion 30 is preferably configured to mate with a corresponding bore in a proximal end of a humeral stem 80 as shown for example in FIGS. 9A-9D. Preferably, trunion 30, 30' has a male taper that may easily be secured to the corresponding tapered bore of humeral stem 80. Other quick-connect mechanisms known in the art may be used to connect cup 10, 10' to a humeral stem, for example, threaded connections, other pressure-fit connections, and clasps.

Proximal end 12, 12' of cup 10, 10' preferably has a substantially flat proximal surface portion 32, 32'. Preferably, proximal surface portion 32, 32' includes a central rounded edge 34, 34' which blends with wall 16, 16' and has a rounded edge 36, 36' which blends with outer surface 24, 24'.

Preferably, surface 32, 32' of humeral cup 10, 10' includes a marker 38, 38' arranged thereon. Marker 38, 38' is preferably of any configuration that gives a user, such as a surgeon or other operating room personnel, a visual frame of reference for the position of an insert with respect to humeral cup 10, 10'.

Figure 3A:
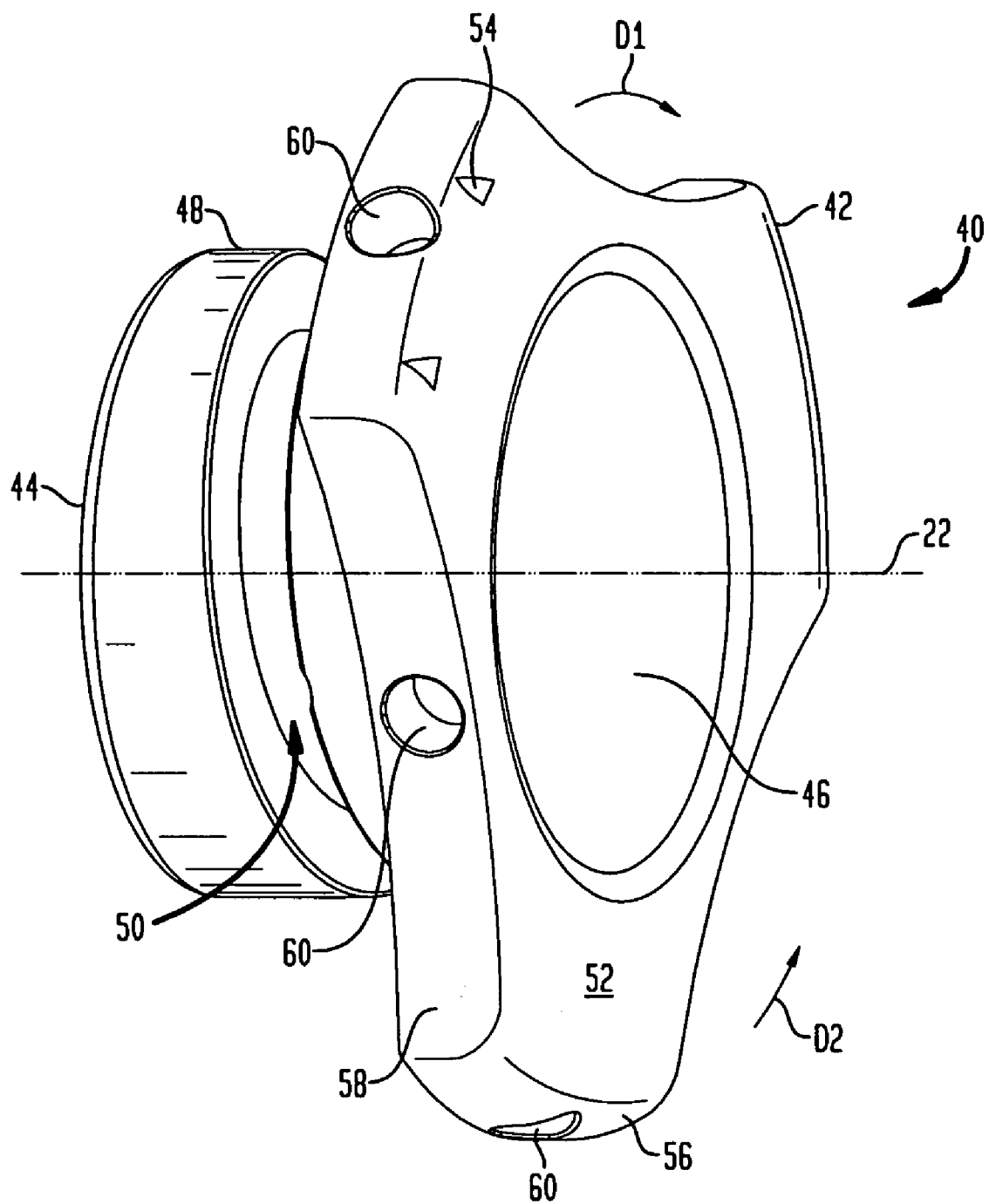
FIG. 3A is an isometric view of an insert according to an embodiment of the present invention.
Figure 3B:
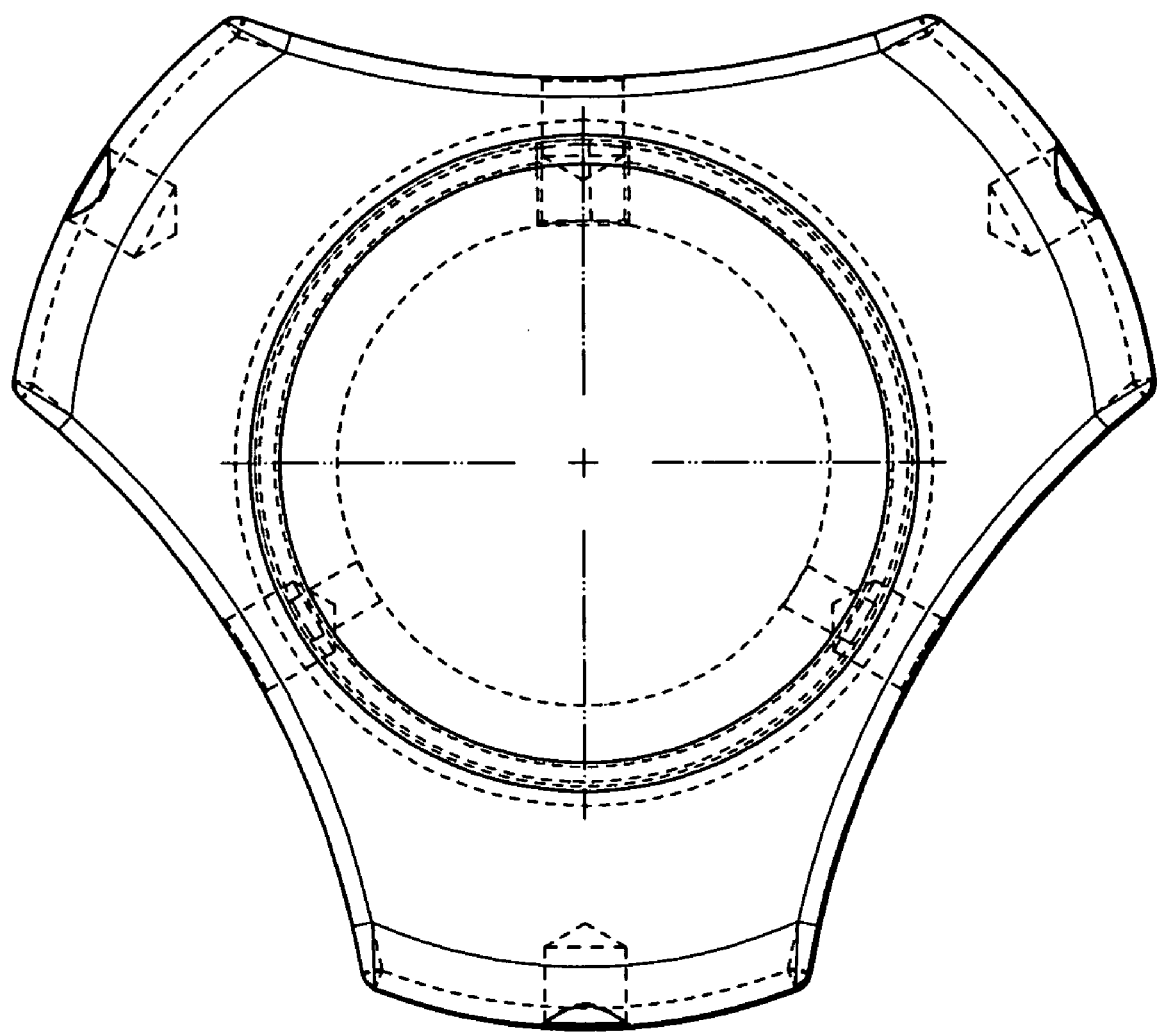
FIG. 3B is a front view of the insert according to FIG. 3A.
Figure 3C:
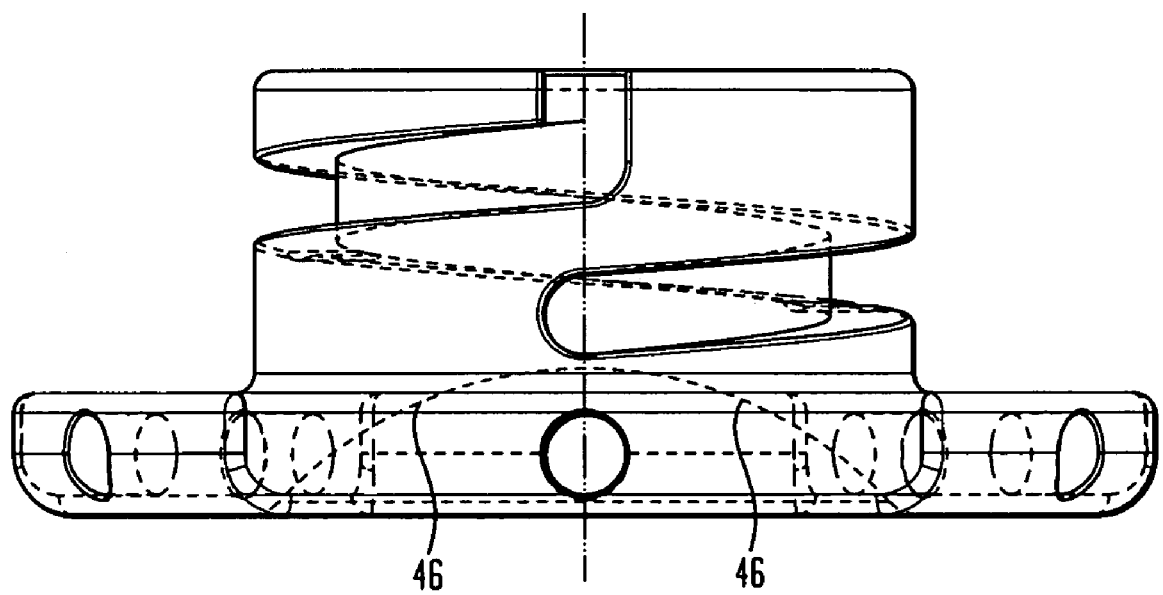
FIG. 3C is a side view of the insert according to FIG. 3A.

Referring to FIGS. 3A-3C, there is shown a first embodiment of the insert of the present invention designated generally by reference numeral 40. Preferably, insert 40 includes a proximal end portion 42 and a distal end 44 portion, the proximal end portion 42 having a proximal surface 52 including a proximally facing concave recessed surface 46 therein. Preferably, distal end portion 44 of insert 40 includes a shaft 48, the shaft having a helical groove 50 disposed on at least a portion thereof. Guide pin 23, 23' protruding from circular wall 16, 16' into recess 20, 20' is configured to engage helical groove 50 of shaft 48 such that while guide pin 23, 23' is engaged with helical groove 50 at least a portion of shaft 48 is located within recess 20, 20'.

Figure 4A:
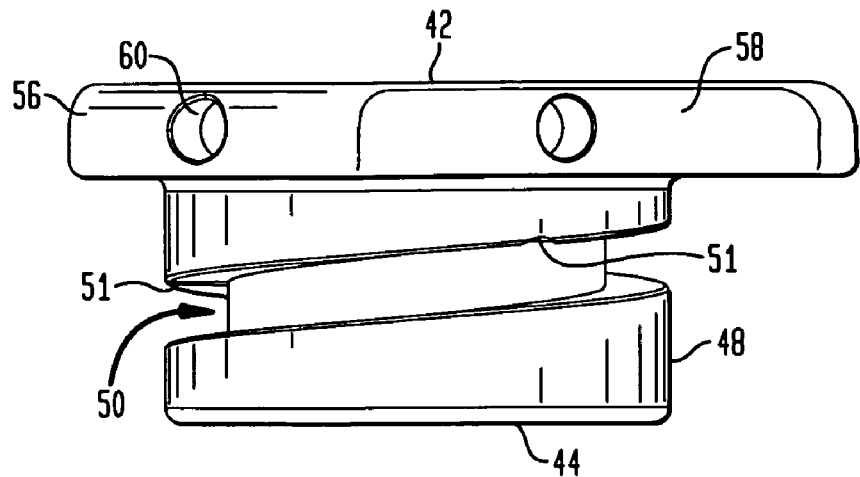
FIG. 4A is a side view of an alternative embodiment of an insert according to the present invention.
Figure 4B:
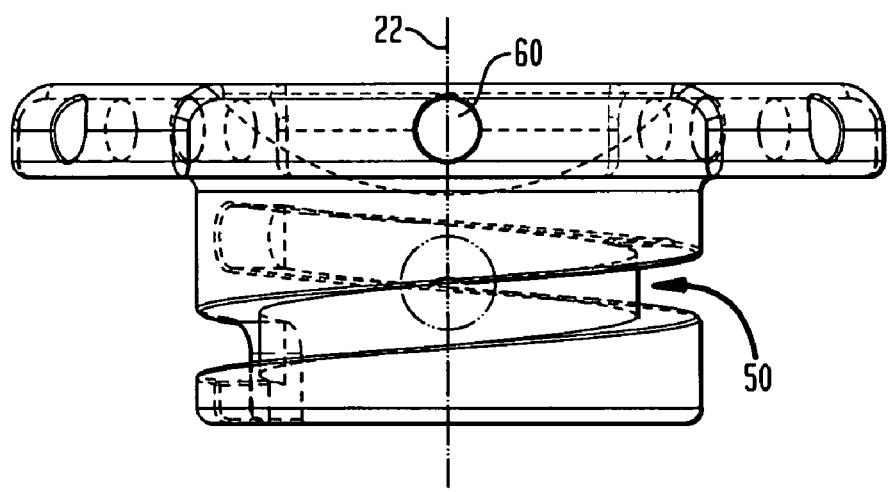
FIG. 4B is a side view of the insert according to FIG. 4A rotated to the left.
Figure 4C:
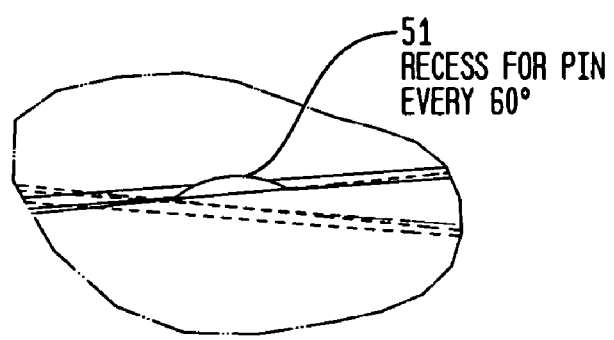
FIG. 4C is a detail view A of a section of the insert according to FIG. 4B.
Figure 5A:
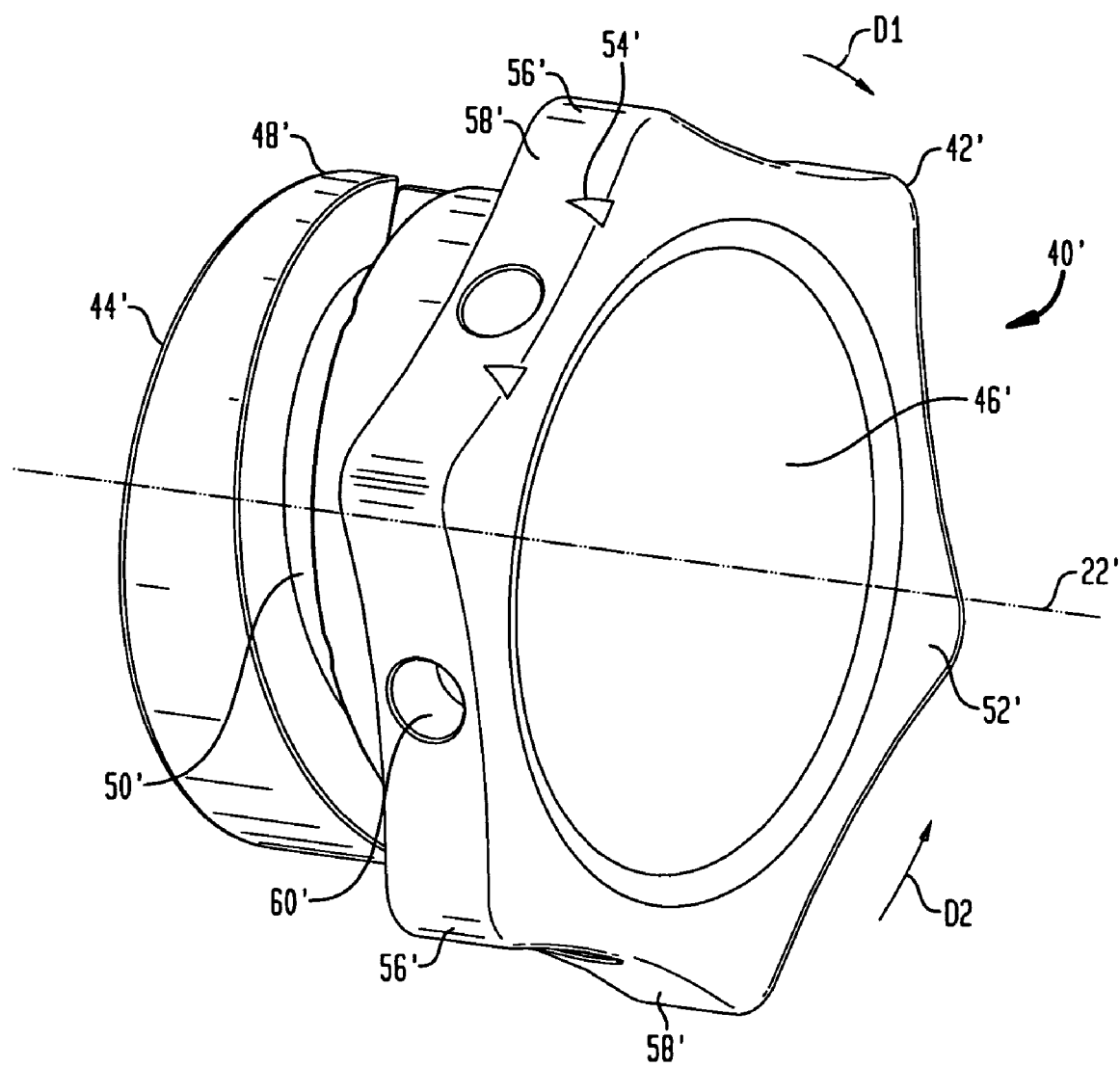
FIG. 5A is an isometric view of an alternative embodiment of an insert of the present invention.
Figure 5B:
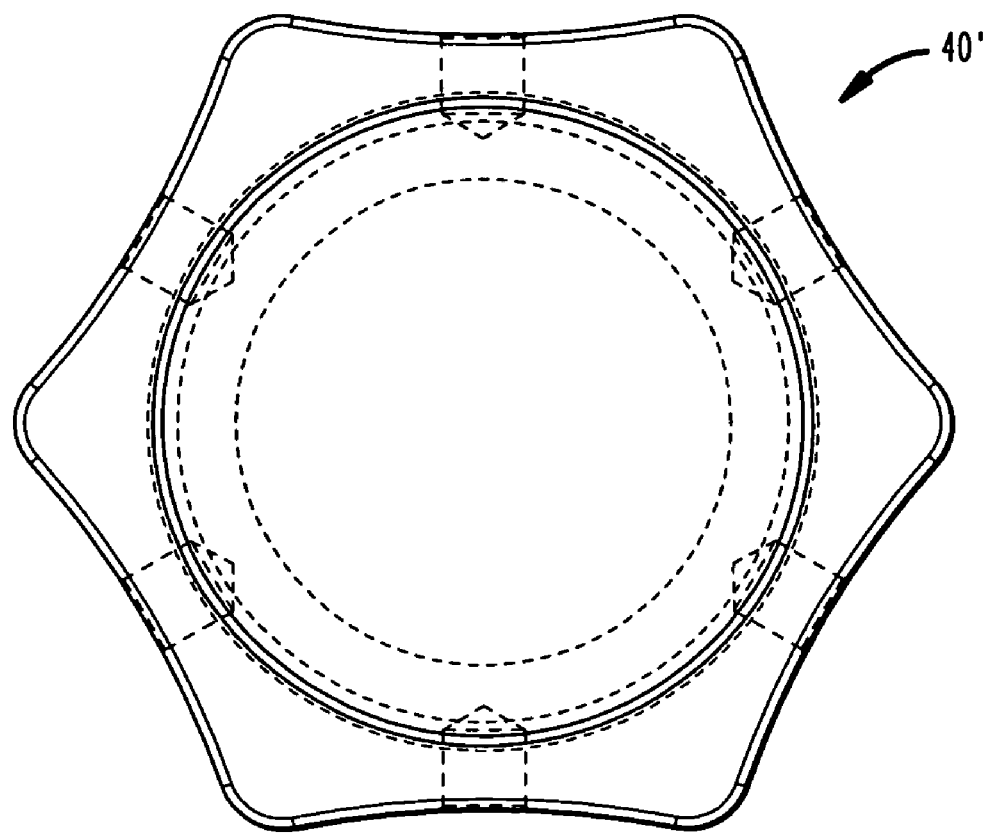
FIG. 5B is a front view of the insert according to FIG. 5A.
Figure 5C:
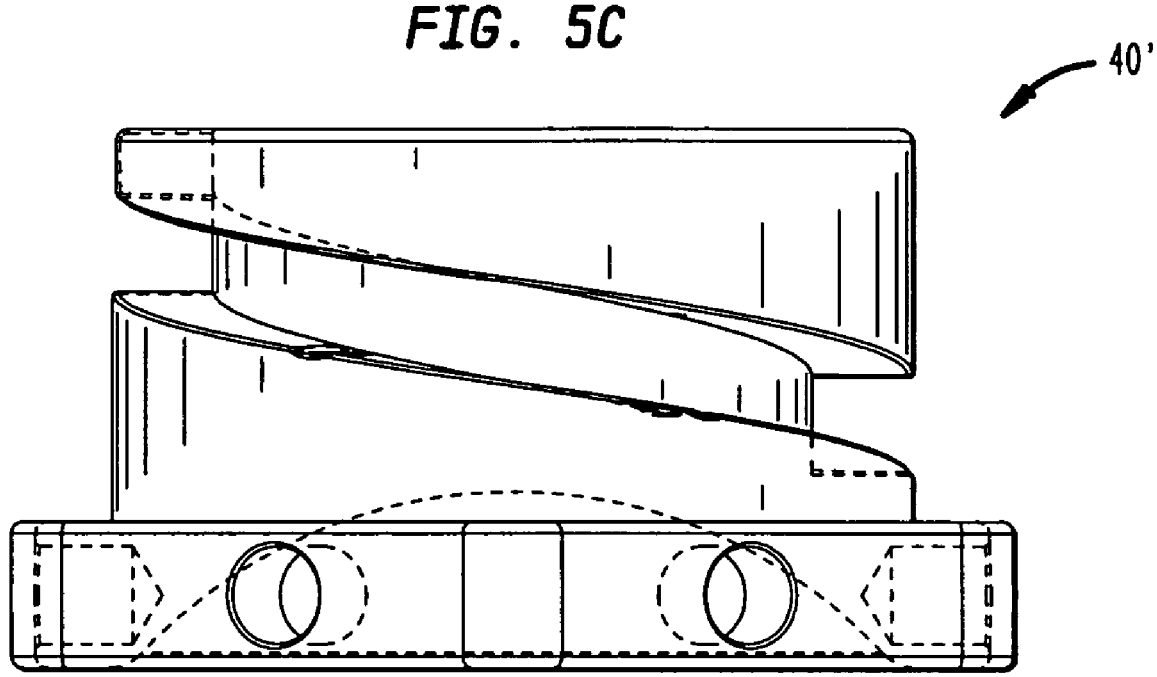
FIG. 5C is a side view of the insert according to FIG. 5A.
Figure 5D:
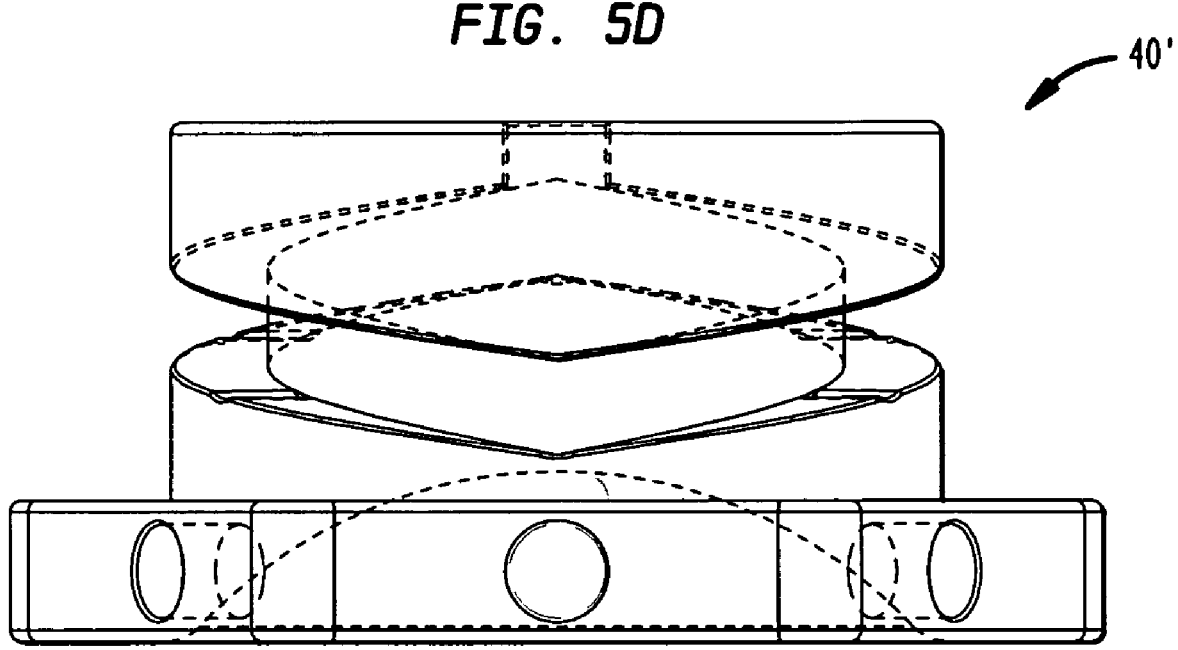
FIG. 5D is a side view of the insert similar to FIG. 5C but rotated to the left.

As shown in FIGS. 4A and 4B, an alternative embodiment of insert 40 may include a plurality of incremental stopping features or indents 51 along groove 50. In a preferred embodiment, each indent 51 is located approximately every 60° along groove 50. As insert 40 having indents 51 is rotated in a first or second direction D1, D2, guide pin 23, 23' of cup 10, 10' may engage an indent 51 of insert 40. Indent 51 is configured to stop insert 40 from further rotation until a force great enough to overcome the friction between guide pin 23, 23' and indent 51 is produced.

Preferably, insert 40 may be rotatably adjusted about axis 22 by rotating in a first direction D1 as generally depicted on FIG. 3A, such that insert 40 may move into recess 20, 20' of humeral cup 10, 10'. Alternatively, insert 40 may be rotatably adjusted about axis 22 in an opposite second direction D2, such that insert 40 may move out of recess 20, 20' of humeral cup 10, 10'. Preferably, the axial distance between proximal end 12, 12' of humeral cup 10, 10' and proximal surface 52 of proximal end portion 42 of insert 40 is adjusted along axis 22 by rotating insert 40 in either first and/or second directions D1, D2.

Figure 7A:
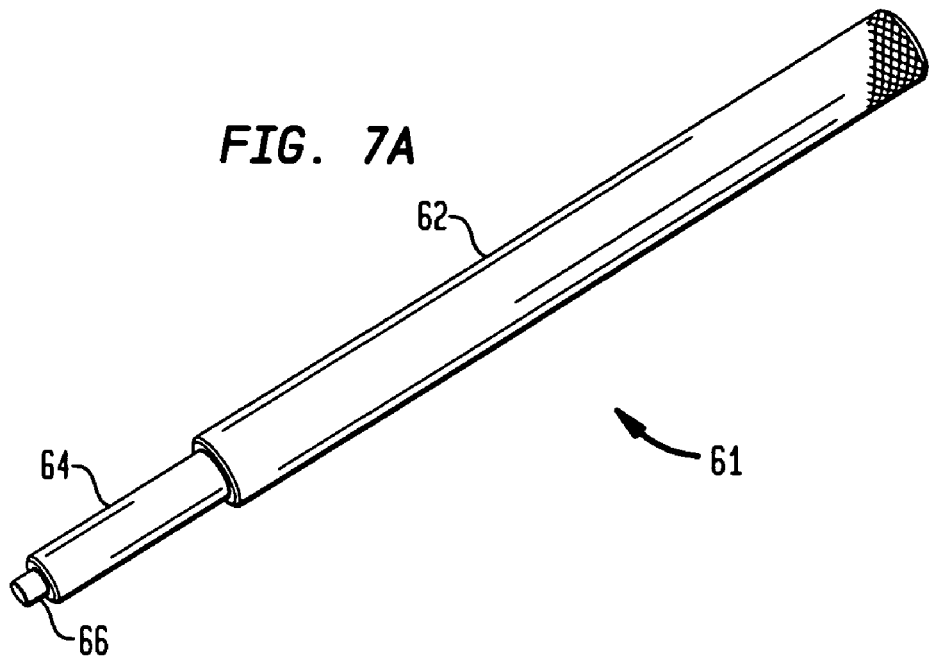
FIG. 7A is an isometric view of an adjustment tool according to an embodiment of the present invention.
Figure 7B:
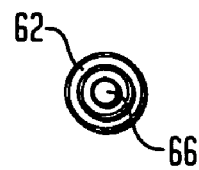
FIG. 7B is a front view of the adjustment tool according to FIG. 7A rotated 180°.
Figure 7C:
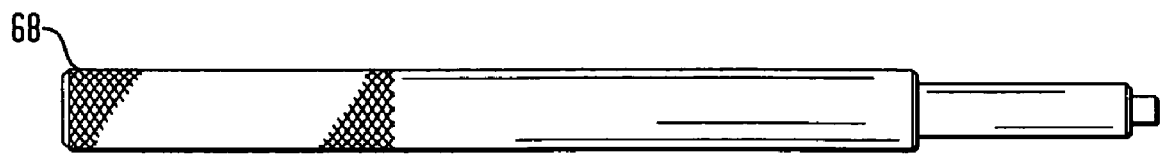
FIG. 7C is a side view of the adjustment tool according to FIG. 7A from the left side.
Figure 9A:
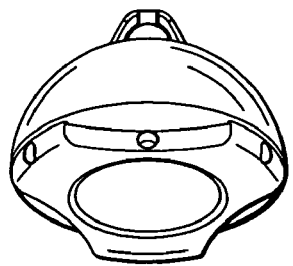
FIG. 9A is an assembled view of the humeral cup of FIG. 1A and the insert of FIG. 3A in a fully collapsed or neutral position.
Figure 9B:
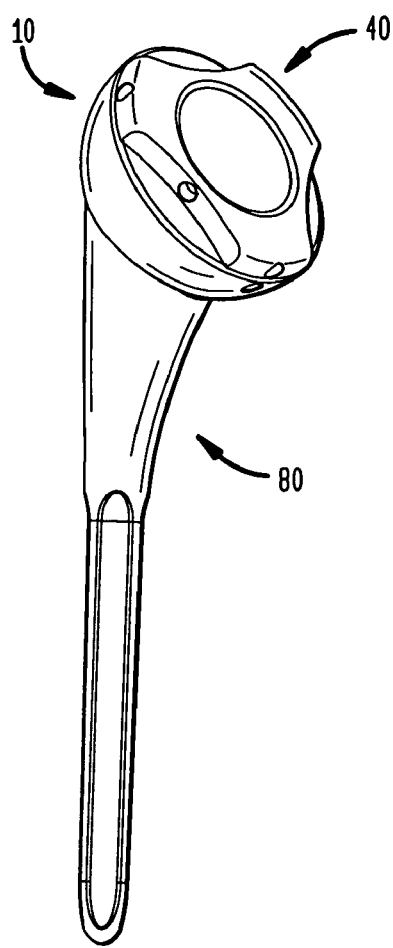
FIG. 9B is an assembled isometric view of the humeral cup and insert of FIG. 9A assembled to an exemplary humeral stem.
Figure 9C:
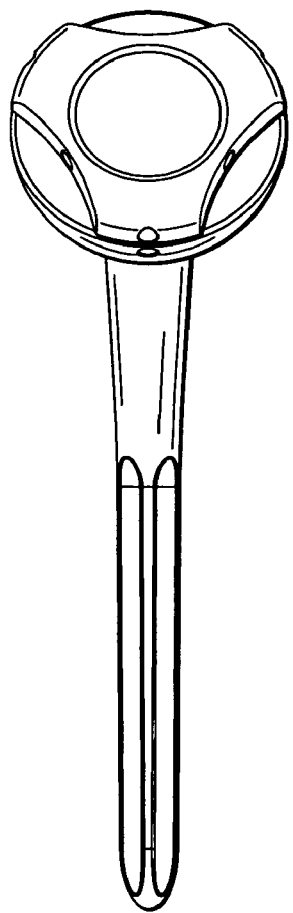
FIG. 9C is an assembled front view of the humeral cup, insert, and humeral stem according to FIG. 9B.
Figure 9D:
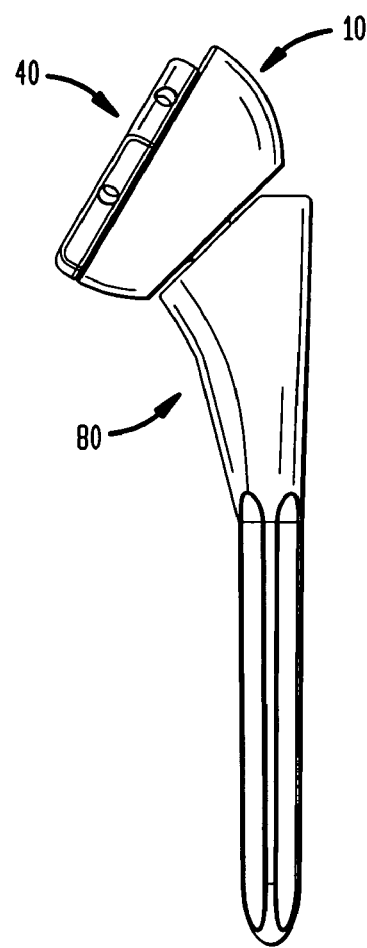
FIG. 9D is an assembled side view of the humeral cup, insert, and humeral stem according to FIG. 9C.
Figure 10A:
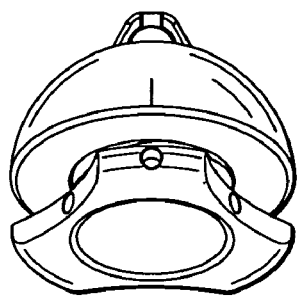
FIG. 10A is an assembled view of the humeral cup of FIG. 1A and the insert of FIG. 3A in an expanded position.
Figure 10B:
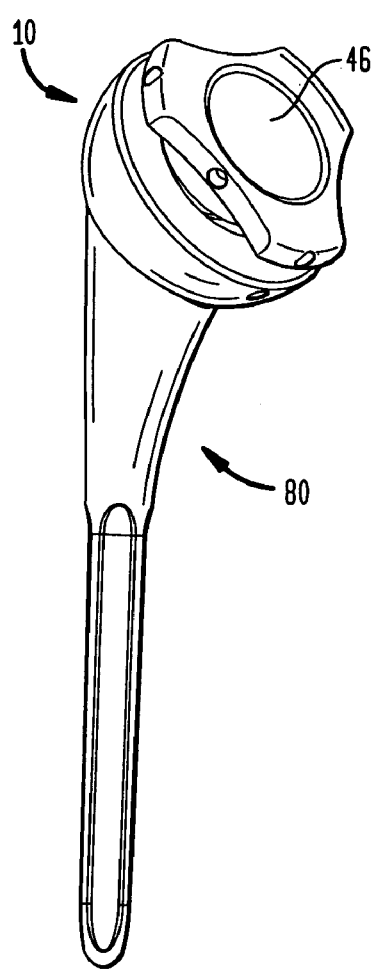
FIG. 10B is an assembled isometric view of the humeral cup and insert of FIG. 10A assembled to an exemplary humeral stem.
Figure 10C:
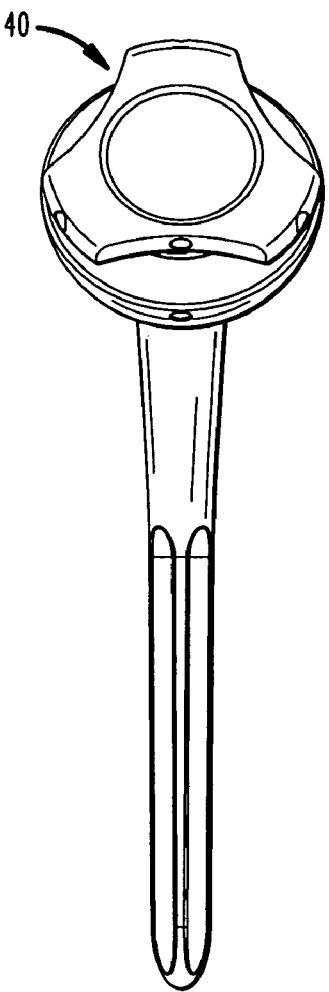
FIG. 10C is an assembled front view of the humeral cup, insert, and humeral stem according to FIG. 10B.
Figure 10D:
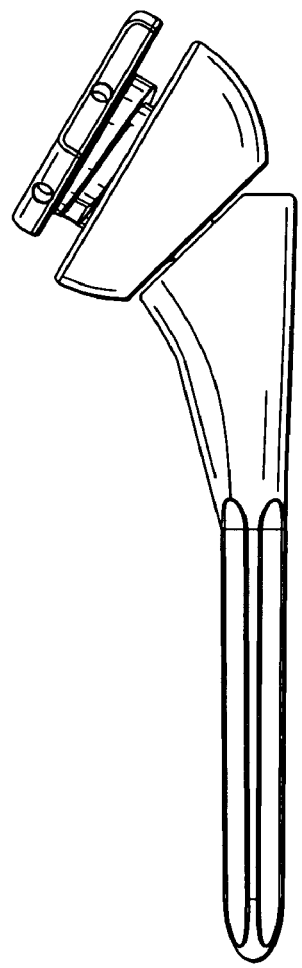
FIG. 10D is an assembled side view of the humeral cup, insert, and humeral stem according to FIG. 10C.

As shown in FIG. 3A, proximal end surface 52 preferably includes a plurality of calibration marks 54 arranged thereon. Preferably, proximal end portion 42 of insert 40 further includes a plurality of alternating convex and concave side faces, 56 and 58 respectively. As shown in FIG. 3A, calibration marks 54 may extend from proximal surface 52 onto side faces 56, 58. Side faces 56, 58 may further include a plurality of attachment locations 60 therein. Preferably, attachment locations 60 are adapted to receive an adjustment tool 61 shown generally in FIGS. 7A-7C. A surgeon or any other operating room personnel may use adjustment tool 61 to rotate insert 40 along axis 22 in either the first and/or second directions D1, D2.

Preferably, adjustment tool 61 includes a handle portion 62 having a shaft 64 protruding therefrom, the shaft having a tip 66 protruding therefrom. Handle portion 62 may further include a knurled portion 68 for easy gripping. It is contemplated by the present invention that tool 61 may have many alternative configurations. Tool 61 is an exemplary instrument for easily rotating insert 40 along axis 22 in either the first and/or second directions D1, D2.

As stated above, calibration marks 54 of insert 40 may also be arranged on side faces 56, 58. Preferably, the axial distance between proximal end 12, 12' of humeral cup 10, 10' and surface 52 of proximal end portion 42 of insert 40 is measured by calibration marks 54 on any of surfaces 52, 56, and 58 of insert 40 in reference to marker 38, 38' of humeral cup 10, 10'.

For example, marker 38, 38' of humeral cup 10, 10' may be lined up with one of the calibration marks 54 of insert 40. Preferably, insert 40 may then be rotated in direction D1 approximately 60° to reduce the distance between proximal end 12, 12' of humeral cup 10, 10' and proximal end surface 52 of insert 40 approximately 2 mm. Insert 40 may then be rotated another 60° in direction D1 until a second calibration mark 54 to the left of the calibration mark 54 is now instead lined up with marker 38, 38' of humeral cup 10, 10'. In this case, the distance between proximal end 12, 12' of humeral cup 10, 10' and proximal end surface 52 of insert 40 would be further reduced approximately 2 mm for a total of 4 mm.

One skilled in the art would understand that the distance between calibration marks may be less than or greater than 60° apart. Preferably, calibration marks are between 30° and 1200 apart. More preferably, calibration marks are between 30° and 600 apart. Further, one skilled in the art would understand that the pitch of groove 50 determines the distance that insert 40 collapses or expands between calibration marks. Preferably, the distance between proximal end 12, 12' of humeral cup 10, 10' and proximal end surface 52 of insert 40 may be reduced or expanded 0.5 mm to 4 mm between calibration marks 54. Further, an exact number of calibration marks 54 would not be needed to indicate a distance X that insert 40 may travel in moving from the fully collapsed or neutral position as shown for example in FIGS. 9A-9D, to an expanded position, shown generally in FIGS. 10A-10D. For example, if the surgeon determines that proper deltoid tension has occurred after expanding the trial approximately 11 mm, attachment locations 60 may be located between calibration marks 54. In this case, the surgeon may approximate the distance insert 40 has collapsed or expanded.

In the preferred embodiment, insert 40 may collapse and/or expand between 0 and 12 mm. More preferably, insert 40 may collapse or expand 6 mm. It is contemplated in the present invention that more or less than six calibration marks 54 may be arranged on insert 40.

Figure 11A:
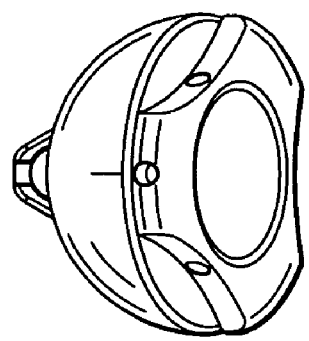
FIG. 11A is an assembled view of the humeral cup of FIG. 2A and the insert of FIG. 3A in a fully collapsed or neutral position.
Figure 11B:
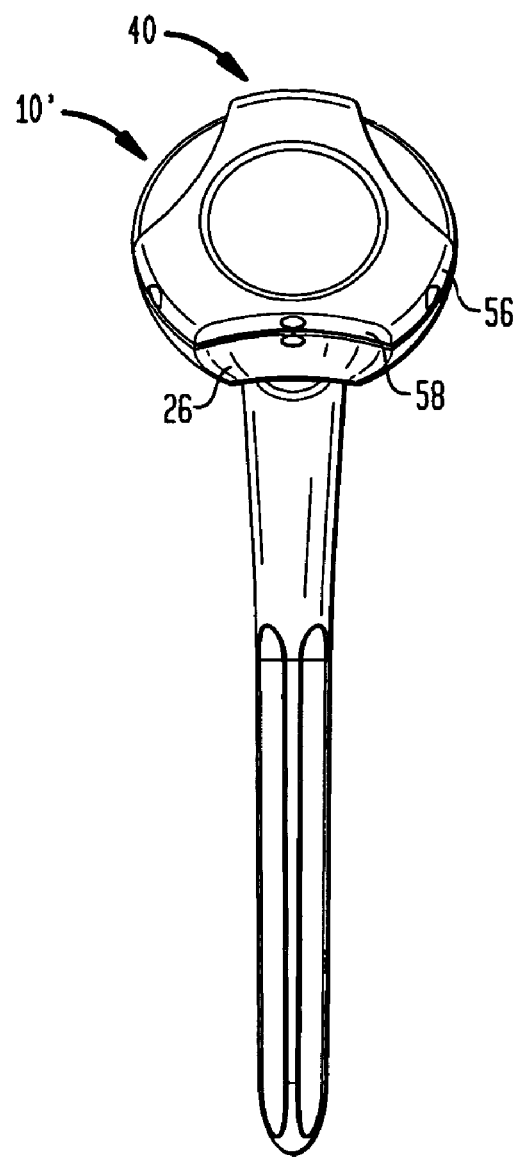
FIG. 11B is an assembled front view of the humeral cup and insert of FIG. 11A assembled to an exemplary humeral stem.
Figure 11C:
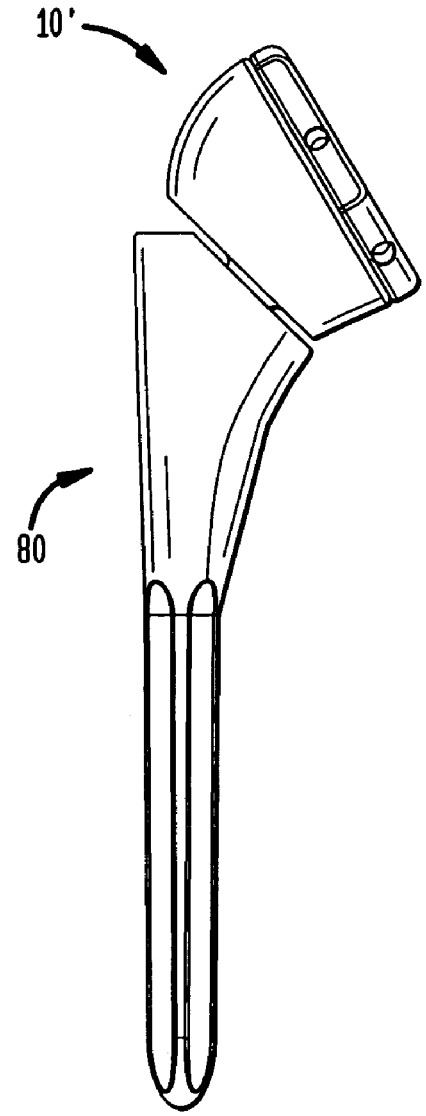
FIG. 11C is an assembled side view of the humeral cup, insert, and humeral stem according to FIG. 11B.
Figure 12A:
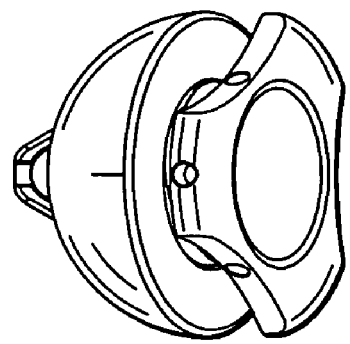
FIG. 12A is an assembled view of the humeral cup of FIG. 2A and the insert of FIG. 3A in an expanded position.
Figure 12B:
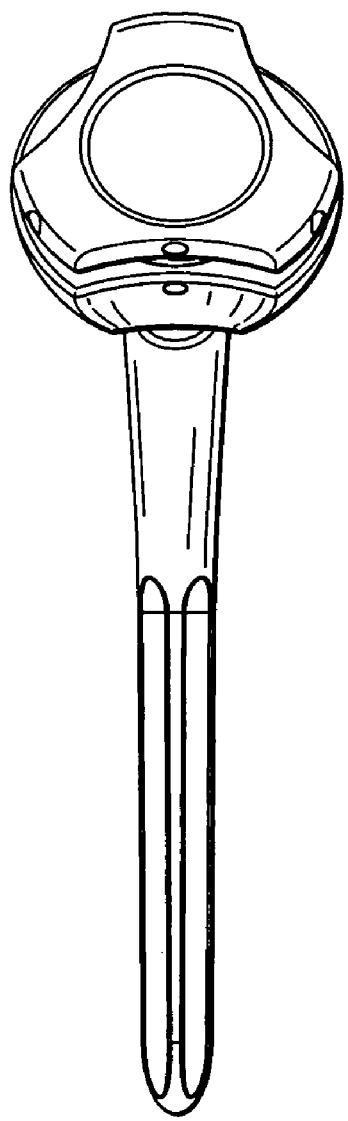
FIG. 12B is an assembled front view of the humeral cup and insert of FIG. 12A assembled to an exemplary humeral stem.
Figure 12C:
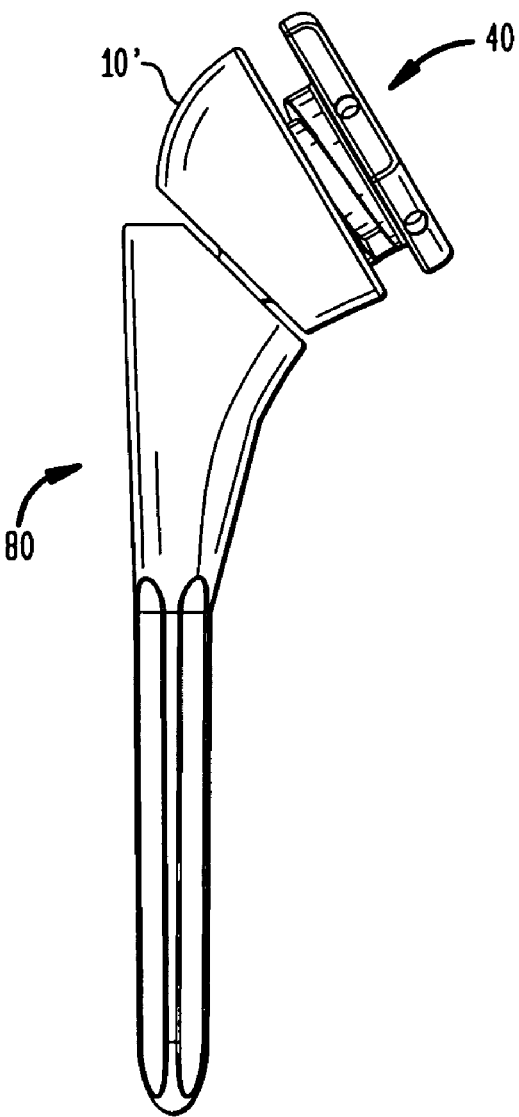
FIG. 12C is an assembled side view of the humeral cup, insert, and humeral stem according to FIG. 12B.

Preferably, as shown in FIGS. 11A-11C, a concave side face 58 of insert 40 is configured to align with surface 26 of humeral cup 10'. It is within the scope of the present invention for one of convex surfaces 56 of insert 40 to be located adjacent to bottom surface 26 as well.

An alternative embodiment of insert 40 of the present invention is designated generally by reference numeral 40' as shown in FIGS. 5A-5D. Preferably, insert 40' includes a proximal end portion 42' and a distal end portion 44', the proximal end portion 42' having a proximal surface 52' including a proximally facing concave recessed surface 46' therein. Preferably, distal end portion 44' of insert 40' includes a shaft 48' having a helical groove 50' disposed on at least a portion thereof. Guide pin 23, 23' protruding from circular wall 16, 16' into recess 20, 20' is configured to engage helical groove 50' of shaft 48' such that while guide pin 23, 23' is engaged with helical groove 50' at least a portion of shaft 48' is located within recess 20, 20'.

Figure 6A:
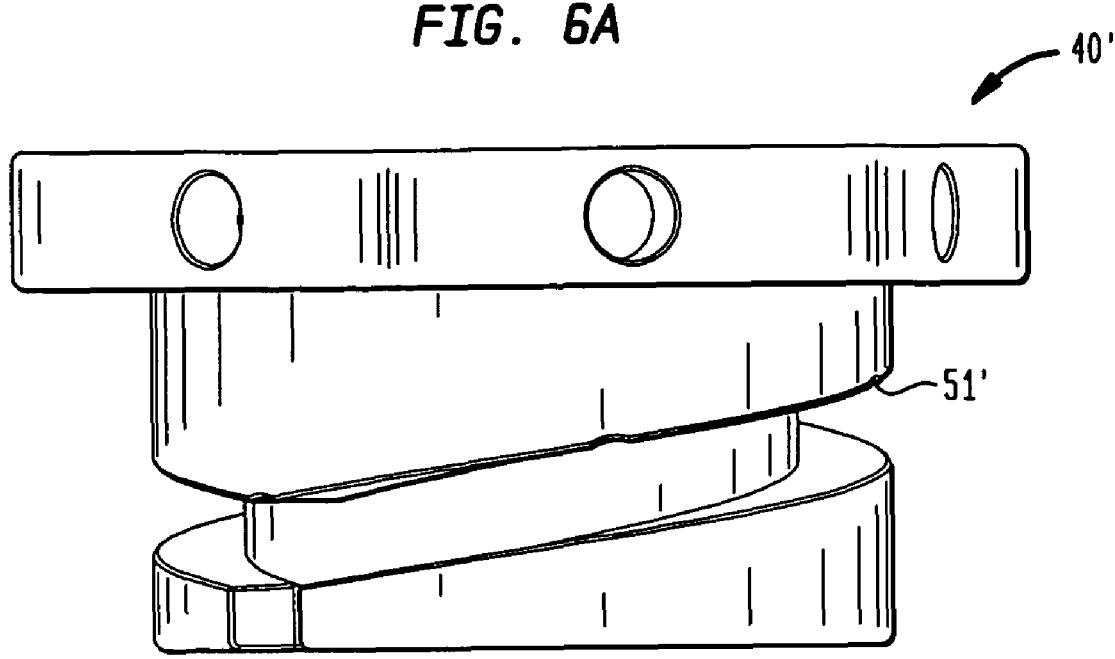
FIG. 6A is a side view of an alternative embodiment of an insert according to the present invention.
Figure 6B:
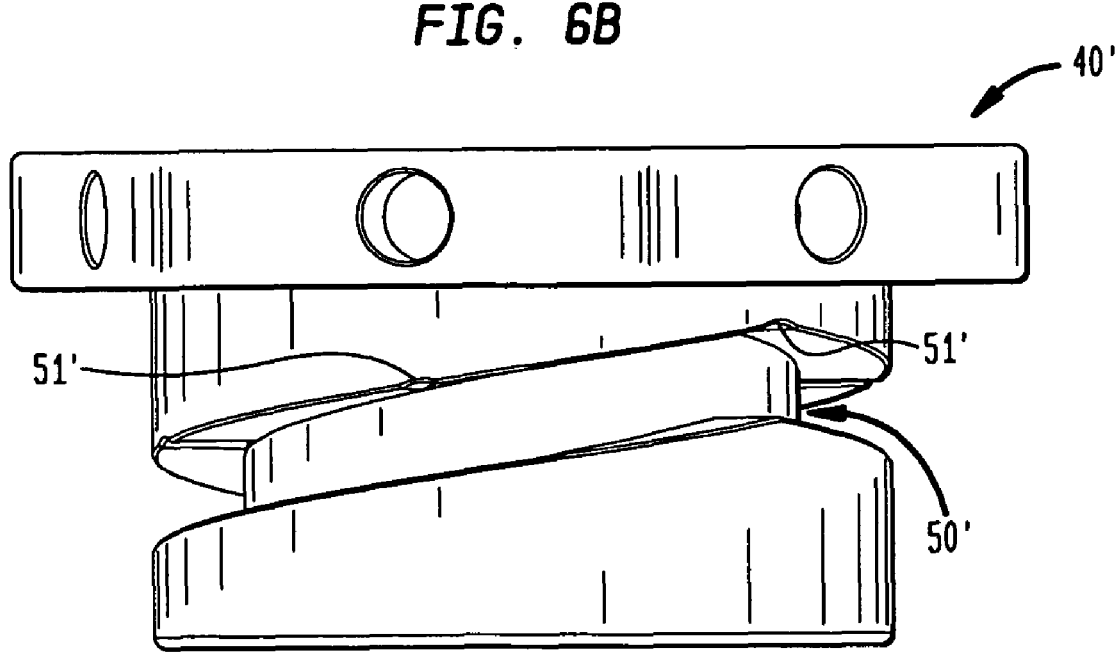
FIG. 6B is a side view of the insert according to FIG. 6A rotated to the left.

As shown in FIGS. 6A and 6B, an alternative embodiment of insert 40' may include a plurality of incremental stopping features or indents 51' along groove 50'. In a preferred embodiment, each indent 51' is located approximately every 60° along groove 50'. As insert 40' having indents 51' is rotated in a first or second direction D1, D2, guide pin 23, 23' of cup 10, 10' may engage an indent 51' of insert 40'. Indent 51' is configured to stop insert 40' from further rotation until a force great enough to overcome the friction between guide pin 23, 23' and indent 51' is produced.

Figure 13A:
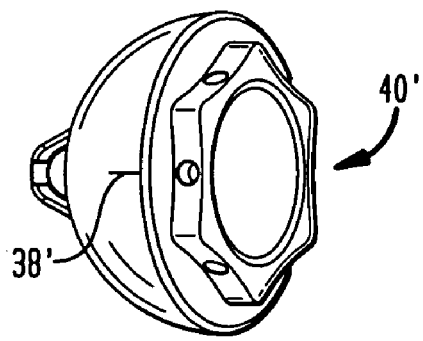
FIG. 13A is an assembled view of the humeral cup of FIG. 2A and the insert of FIG. 5A in a fully collapsed or neutral position.
Figure 13B:
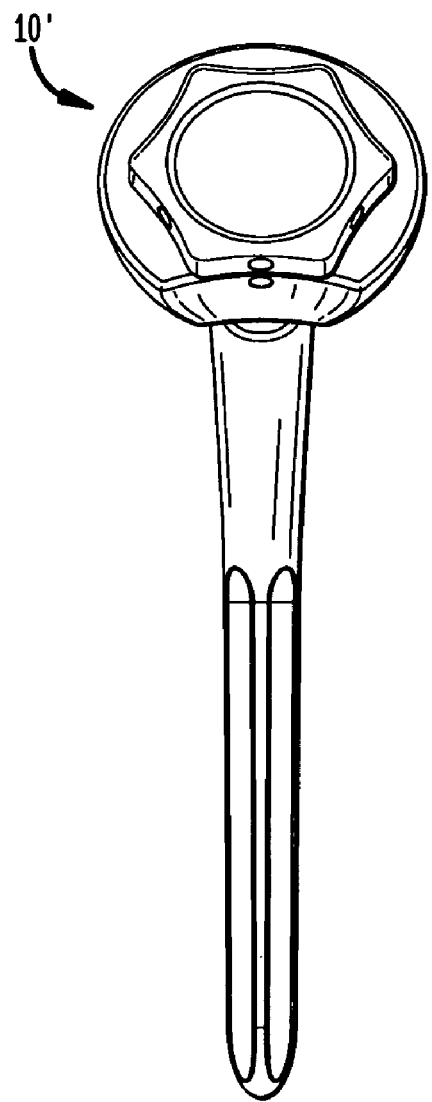
FIG. 13B is an assembled front view of the humeral cup and insert of FIG. 13A assembled to an exemplary humeral stem.
Figure 13C:
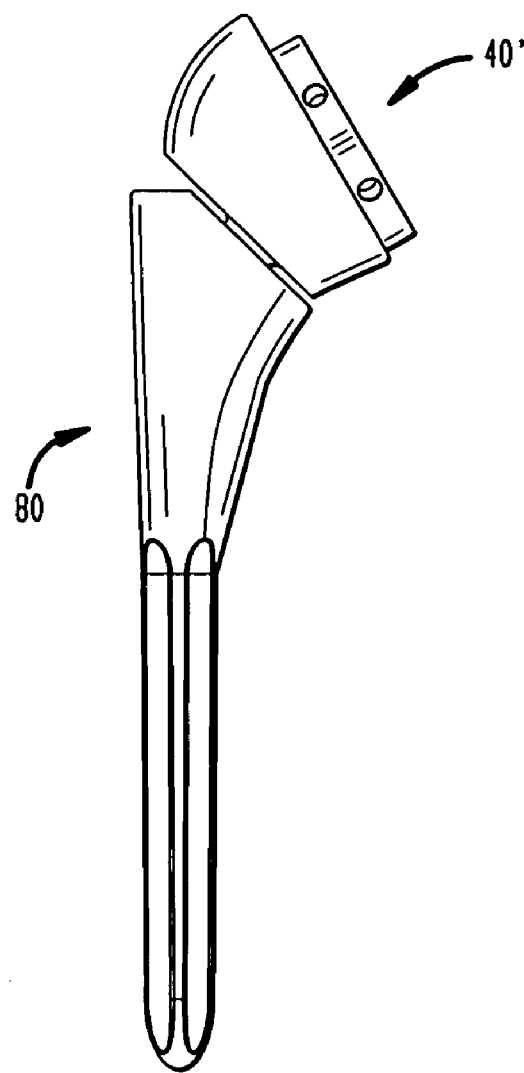
FIG. 13C is an assembled side view of the humeral cup, insert, and humeral stem according to FIG. 13B.
Figure 14A:
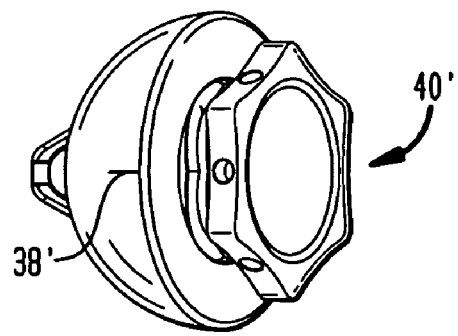
FIG. 14A is an assembled view of the humeral cup of FIG. 2A and the insert of FIG. 5A in an expanded position.
Figure 14B:
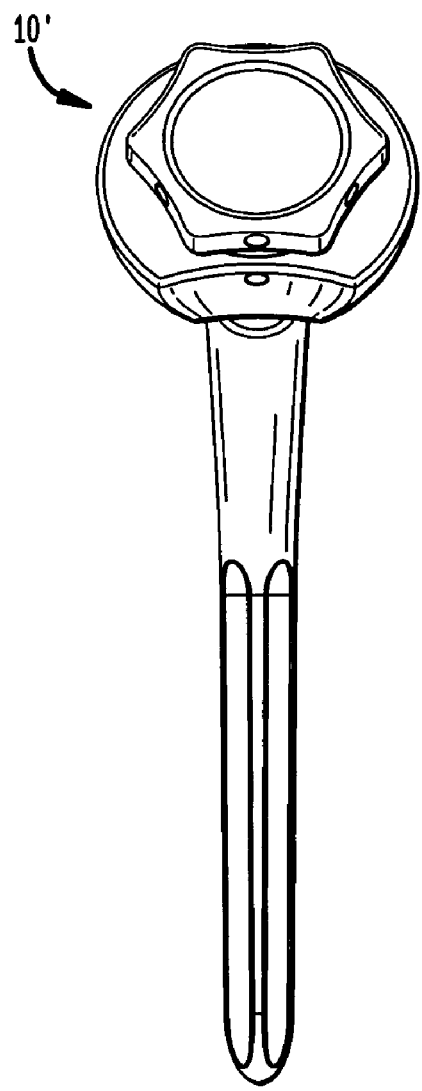
FIG. 14B is an assembled front view of the humeral cup and insert of FIG. 14A assembled to an exemplary humeral stem.
Figure 14C:
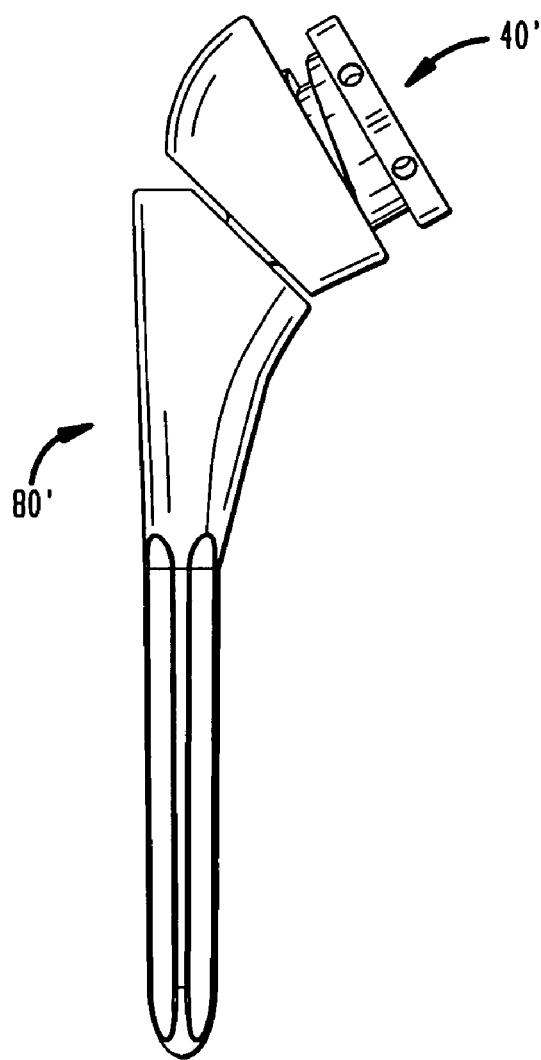
FIG. 14C is an assembled side view of the humeral cup, insert, and humeral stem according to FIG. 14B.

Referring to FIGS. 5A-5D, helical groove 50' of shaft 48' of insert 40' preferably allows proximal end portion 42' of insert 40' to move away from proximal end 12, 12' of humeral cup 10, 10' and thereafter toward proximal end 12, 12' of humeral cup 10, 10' as insert 40' is rotated in only the first direction D1. For example, if insert 40' is in the fully collapsed or neutral position as shown in FIGS. 13A-13C, generally defined by shaft 48' of insert 40' being fully seated in recess 20, 20' a surgeon or other operating room personnel may rotate insert 40' in first direction D1. This rotation will cause shaft 48' of insert 40' to move out of recess 20, 20' wherein proximal end portion 42' will thus move away from proximal end 12, 12' of humeral cup 10, 10'. Eventually, the trial will be in a fully expanded position, shown generally in FIGS. 14A-14C. This is generally the point where an outer surface 52' of proximal end portion 42' is furthest away from proximal end 12, 12' while insert 40' is still assembled or engaged to humeral cup 10, 10'. Because of the configuration of helical groove 50', if insert 40' continues to rotate in first direction D1, proximal end portion 42' will begin to start moving back towards proximal end 12, 12' of humeral cup 10, 10'.

Preferably, proximal surface 52' includes a plurality of calibration marks 54' arranged thereon. Preferably, proximal end portion 42' of insert 40' further includes a plurality of alternating convex and concave side faces, 56' and 58' respectively. Side faces 56', 58' may further include a plurality of attachment locations 60' therein. Preferably, attachment locations 60' are adapted to receive a portion of adjustment tool 61. A surgeon or any other operating room personnel may use adjustment tool 61 to rotate insert 40' along axis 22' in either the first and/or second directions D1, D2.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, the present invention may be applied to hip systems as well.

The invention claimed is:

1. An expandable shoulder trial device comprising:
   an elongate shaft having proximal and distal ends;
   a humeral cup including a distal end portion coupled to the proximal end of the elongate shaft, the humeral cup further including a proximal end portion having an outer surface with a base and a circular wall defining a recess, the wall having a guide pin protruding therefrom; and
   an insert having a proximal end portion and a distal end portion for insertion in the recess, the distal end portion having a cam track extending toward the proximal end portion, the cam track adapted to receive the guide pin of the humeral cup,
   wherein the insert is rotatably adjustable along an axis in a first direction such that the distal end portion of the insert moves toward the base of the recess of the humeral cup until the trial is fully collapsed.

2. The expandable shoulder trial of claim 1, wherein the insert is rotatably adjustable along the axis in an opposite second direction wherein the distal end portion of the insert moves away from the base of the recess of the humeral cup until the trial is fully expanded.

3. The expandable shoulder trial of claim 2, wherein the proximal end portion of the insert includes an outer face having a plurality of calibration marks arranged thereon.

4. The expandable shoulder trial of claim 3, wherein the outer face of the insert includes a plurality of attachment locations adapted to engage an adjustment tool.

5. The expandable shoulder trial of claim 3, wherein the proximal end portion of the humeral cup includes a front face having a marker arranged thereon.

6. The expandable shoulder trial of claim 5, wherein the distance between the proximal end portion of the humeral cup and the proximal end portion of the insert is adjusted by rotating the insert in either the first and or second direction.

7. The expandable shoulder trial of claim 6, wherein the axial distance between the proximal end portion of the humeral cup and the proximal end portion of the insert is indicated by the calibration marks of the insert in reference to the marker of the humeral cup.

8. The expandable shoulder trial of claim 1, wherein rotating the insert in the first direction approximately 60° reduces the distance between the proximal end portion of the humeral cup and the proximal end portion of the insert approximately 2 mm.

9. An expandable trial comprising:
   an insert including a proximal end portion and a shaft portion having a distal end, the proximal end portion having a concave recess therein, the shaft portion having a helical groove disposed on at least a portion thereof about an axis;
   an elongate shaft having proximal and distal ends;
   a humeral cup having a distal end surface and a proximal end, the distal end surface adapted to lie adjacent to the proximal end of the elongate shaft when the humeral cup is coupled to the elongate shaft, the proximal end surface having an outer surface including a recess therein, the recess defined by a circular wall; and
   a guide pin protruding from the circular wall into the recess, the guide pin adapted to engage the helical groove of the shaft portion of the insert;
   wherein the proximal end portion of the insert may be rotatably adjusted in a first direction along the axis toward the proximal end outer surface of the cup and in an opposite direction along the axis away from the proximal end outer surface of the cup by the interaction of the guide pin and the groove.

10. The expandable shoulder trial of claim 9, wherein the helical groove of the shaft allows the insert when rotated to move in the first axial direction until the trial is fully expanded and then in an opposite axial direction until the trial is fully collapsed as the insert is rotated in only a first direction.

11. The expandable shoulder trial of claim 9, wherein the proximal end portion of the insert includes an outer face having a plurality of calibration marks arranged thereon.

12. The expandable shoulder trial of claim 9, wherein an outer face of the insert includes a plurality of attachment locations adapted to be engaged by an adjustment tool.

13. The expandable shoulder trial of claim 11, wherein the proximal end outer surface of the cup has a marker thereon.

14. The expandable shoulder trial of claim 13, wherein the axial distance between the proximal end outer surface of the humeral cup and the proximal end portion of the insert is adjusted by rotating the insert in either the first and or second axial direction.

15. The expandable shoulder trial of claim 14, wherein the axial distance between the proximal end outer surface of the humeral cup and a proximal face of the proximal end portion of the insert is indicated by calibration marks of the insert in reference to the marker of the humeral cup.

16. The expandable shoulder trial of claim 15, wherein the calibration marks are located at 60° increments.

17. The expandable shoulder trial of claim 16, wherein rotating the insert in the first direction approximately 60° reduces the distance between the proximal end outer surface of the humeral cup and the proximal face of the proximal end portion of the insert approximately 2 mm.

18. An expandable shoulder trial comprising:
an elongate shaft having proximal and distal ends;
a humeral cup having distal and proximal end surfaces, an axis and an outer surface having a recess defining a substantially circular wall formed about the axis, the distal end surface adapted to lie adjacent to the proximal end of the shaft when the humeral cup is coupled to the elongate shaft, the recess having a guide portion extending outwardly therefrom;
an insert including a proximal end portion and a shaft portion having a distal end surface, the shaft having a helical groove disposed on at least a portion thereof, the proximal end portion having an end surface having a concave recess disposed thereon;
wherein the guide portion is adapted to engage the helical groove of the shaft so that when the insert is rotatably adjusted the insert moves from a first position wherein the proximal end surface of the insert is substantially closer to the proximal end surface of the humeral cup, and into a second position wherein the proximal end surface of the insert is further away from the proximal end surface of the cup along the axis of the humeral cup.

19. The expandable shoulder trial of claim 18, wherein the helical groove of the shaft allows the insert when rotated to move from the first position to the second position and back towards the first position as the insert is rotated in only a first direction.

20. The expandable shoulder trial of claim 19, wherein the proximal end surface has a plurality of calibration marks arranged thereon.

21. The expandable shoulder trial of claim 18, wherein the proximal end surface of the insert includes a plurality of attachment locations adapted to engage an adjustment device.

22. The expandable shoulder trial of claim 20, wherein the proximal end surface of the humeral cup has a marker thereon.

23. The expandable shoulder trial of claim 22, wherein the distance between the proximal end surface of the humeral cup and the proximal end surface of the insert is adjusted by rotating the insert in either the first and or second direction.

24. The expandable shoulder trial of claim 23, wherein the axial distance between the proximal end surface of the humeral cup and the proximal end portion of the insert is indicated by the calibration marks of the insert in reference to the marker of the humeral cup.

25. The expandable shoulder trial of claim 18, wherein rotating the insert in the first direction approximately 60° reduces the distance between the proximal end surface of the humeral cup and the proximal end surface of the insert approximately 2 mm.

* * * * *